(12) United States Patent
Govari et al.

(10) Patent No.: US 12,336,803 B2
(45) Date of Patent: Jun. 24, 2025

(54) ASSESSING TISSUE CONTACT WITH CATHETER USING PAIRS OF ELECTRODES AND COMMON REFERENCE GROUND ESTABLISHED USING DESIGNED CIRCUIT-BOARD CAPACITANCE

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 367 days.

(21) Appl. No.: 17/986,107

(22) Filed: Nov. 14, 2022

(65) Prior Publication Data

US 2023/0089455 A1 Mar. 23, 2023

Related U.S. Application Data

(62) Division of application No. 16/055,810, filed on Aug. 6, 2018, now Pat. No. 11,523,750.

(51) Int. Cl.
*A61B 18/12* (2006.01)
*A61B 5/0538* (2021.01)
(Continued)

(52) U.S. Cl.
CPC ............ *A61B 5/068* (2013.01); *A61B 5/0538* (2013.01); *A61B 5/063* (2013.01);
(Continued)

(58) Field of Classification Search
CPC ...... A61B 18/12; A61B 18/1206; A61B 18/14; A61B 18/1402; A61B 18/1492; A61B 2018/00351; A61B 2018/00577; A61B 2018/00648; A61B 2018/00666; A61B 2018/00875; A61B 2018/00357;
(Continued)

(56) References Cited

U.S. PATENT DOCUMENTS 6,391,024 B1    5/2002   Sun et al.
8,267,926 B2    9/2012   Paul et al.
(Continued)

OTHER PUBLICATIONS

Japanese OA for corresponding appln. No. 2019-143567 dated Jul. 14, 2023.
(Continued)

*Primary Examiner* — Thomas A Giuliani

(57) ABSTRACT

An apparatus includes a current source, an electronic circuit and a circuit board. The current source is configured to flow an electrical current having a selected frequency between a pair of electrodes coupled to a medical probe. The electronic circuit is configured to measure a single-ended voltage relative to ground that is formed on at least one of the electrodes in the pair in response to the electrical current, and, based on the measured voltage, to assess physical contact between the at least one of the electrodes and tissue. The circuit board includes the current source and the electronic circuit, and includes a layout that produces, at the selected frequency, a predefined capacitance between the current source and ground, thus forming a reference for measurement of the single-ended voltage.

6 Claims, 2 Drawing Sheets

(51) Int. Cl.
*A61B 5/06* (2006.01)
*A61B 18/14* (2006.01)
*A61B 5/00* (2006.01)
*A61B 18/00* (2006.01)

(52) U.S. Cl.
CPC .......... *A61B 18/1206* (2013.01); *A61B 18/14* (2013.01); *A61B 5/062* (2013.01); *A61B 5/6852* (2013.01); *A61B 2018/00351* (2013.01); *A61B 2018/00577* (2013.01); *A61B 2018/00648* (2013.01); *A61B 2018/00666* (2013.01); *A61B 2018/00875* (2013.01); *A61B 2560/0223* (2013.01)

(58) Field of Classification Search
CPC ........... A61B 2018/00755; A61B 2018/00636; A61B 2018/00642; A61B 2018/0072; A61B 2018/00892; A61B 2018/1467; A61B 2090/065; A61B 5/0538; A61B 5/6852; A61B 5/6886
USPC ..... 606/34, 38, 41, 42; 607/98, 99, 115, 116
See application file for complete search history.

(56) References Cited

U.S. PATENT DOCUMENTS

| | | |
|---|---|---|
| 8,456,182 B2 | 6/2013 | Bar-Tal et al. |
| 9,952,169 B2 | 4/2018 | Son et al. |
| 2008/0281319 A1 | 11/2008 | Paul et al. |
| 2008/0312713 A1* | 12/2008 | Wilfley .................. A61B 5/053 606/41 |
| 2013/0324933 A1 | 12/2013 | Wilmot |
| 2013/0324993 A1 | 12/2013 | Mccarthy et al. |
| 2014/0051959 A1 | 2/2014 | Gliner et al. |
| 2014/0346715 A1 | 11/2014 | Lengsfeld |
| 2014/0364715 A1 | 12/2014 | Hauck |
| 2015/0141798 A1 | 5/2015 | Bar-Tal |
| 2016/0143686 A1 | 5/2016 | Tunay et al. |
| 2016/0287137 A1* | 10/2016 | Condie ................. A61B 5/6869 |
| 2017/0333720 A1 | 11/2017 | Astrom et al. |
| 2020/0037924 A1 | 2/2020 | Govari et al. |

OTHER PUBLICATIONS

Extended European Search Report, received for European Application No. 19190009.1, dated Dec. 11, 2019, 11 pages.

* cited by examiner

ASSESSING TISSUE CONTACT WITH CATHETER USING PAIRS OF ELECTRODES AND COMMON REFERENCE GROUND ESTABLISHED USING DESIGNED CIRCUIT-BOARD CAPACITANCE

This patent application is a divisional of U.S. patent application Ser. No. 16/055,810 filed on Aug. 6, 2018, now U.S. Pat. No. 11,523,750, issued on Dec. 13, 2022.

FIELD OF THE INVENTION

The present invention relates generally to invasive medical devices, and particularly to methods and systems for assessing contact between catheter and tissue.

BACKGROUND OF THE INVENTION

In various medical procedures, such as in ablation of heart tissue, a physician needs to know the extent of physical contact between a medical probe and tissue when performing a medical procedure to the tissue. Various techniques for determining proximity and contact are known in the art.

For example, U.S. Patent Application Publication 2016/0143686 describes a method of determining the distance between an electrode catheter disposed in a body fluid adjacent an internal body surface, and the internal body surface, the method includes applying an alternating voltage or an alternating current, determining the impedance between at least one pair of electrodes on the electrode catheter, and determining the distance between the electrode catheter and the internal body surface based at least in part on the determined impedance.

U.S. Patent Application Publication 2016/0287137 describes a method and system for assessing electrode-tissue contact before the delivery of ablation energy. The method includes determining a difference between a maximum impedance magnitude at a low frequency for a given electrode and an absolute minimum impedance magnitude at the low frequency across all electrodes. The method further includes determining a difference between a maximum impedance magnitude at a high frequency for a given electrode and an absolute minimum impedance magnitude at the high frequency across all electrodes, and determining a difference between a maximum impedance phase at the high frequency for a given electrode and an absolute minimum impedance phase at the high frequency across all electrodes.

SUMMARY OF THE INVENTION

An embodiment of the present invention that is described herein provides an apparatus that includes a current source, an electronic circuit and a circuit board. The current source is configured to flow an electrical current having a selected frequency between a pair of electrodes coupled to a medical probe. The electronic circuit is configured to measure a single-ended voltage relative to ground that is formed on at least one of the electrodes in the pair in response to the electrical current, and, based on the measured voltage, to assess physical contact between the at least one of the electrodes and tissue. The circuit board includes the current source and the electronic circuit, and includes a layout that produces, at the selected frequency, a predefined capacitance between the current source and ground, thus forming a reference for measurement of the single-ended voltage.

In some embodiments, the electronic circuit includes an application specific integrated circuit (ASIC). In other embodiments, the electrodes of the pair are fixed at opposite ends of a first section of the medical probe, and include an additional current source, which is configured to flow the electrical current between an additional pair of electrodes coupled to opposite ends of a second section of the medical probe, different from the first section, each of the additional electrodes is electrically coupled to the electronic circuit so as to assess physical contact between at least one of the additional electrodes and tissue. In yet other embodiments, the apparatus includes a processor, which is configured, based on the assessed physical contacts, to output whether there is physical contact between the tissue and at least one of (i) the electrodes, and (ii) the additional electrodes.

In an embodiment, the first and second sections are not overlapped with one another. In another embodiment, the electronic circuit is configured to indicate that the at least one of the electrodes is in physical contact with the tissue when the measured voltage is above a predefined threshold, and to indicate that the at least one of the electrodes is not in physical contact with the tissue when the measured voltage is below the predefined threshold.

There is additionally provided, in accordance with an embodiment of the present invention, a method including flowing from a current source an electrical current having a selected frequency between a pair of electrodes coupled to a medical probe. Using an electronic circuit, a single-ended voltage is measured relative to ground that is formed on at least one of the electrodes in the pair in response to the electrical current, and, based on the measured voltage, physical contact between the at least one of the electrodes and tissue is assessed. A circuit board, which includes the current source and the electronic circuit includes a layout that produces, at the selected frequency, a predefined capacitance between the current source and ground, thus forming a reference for measurement of the single-ended voltage.

The present invention will be more fully understood from the following detailed description of the embodiments thereof, taken together with the drawings in which:

DETAILED DESCRIPTION OF EMBODIMENTS

Overview

Figure 1:
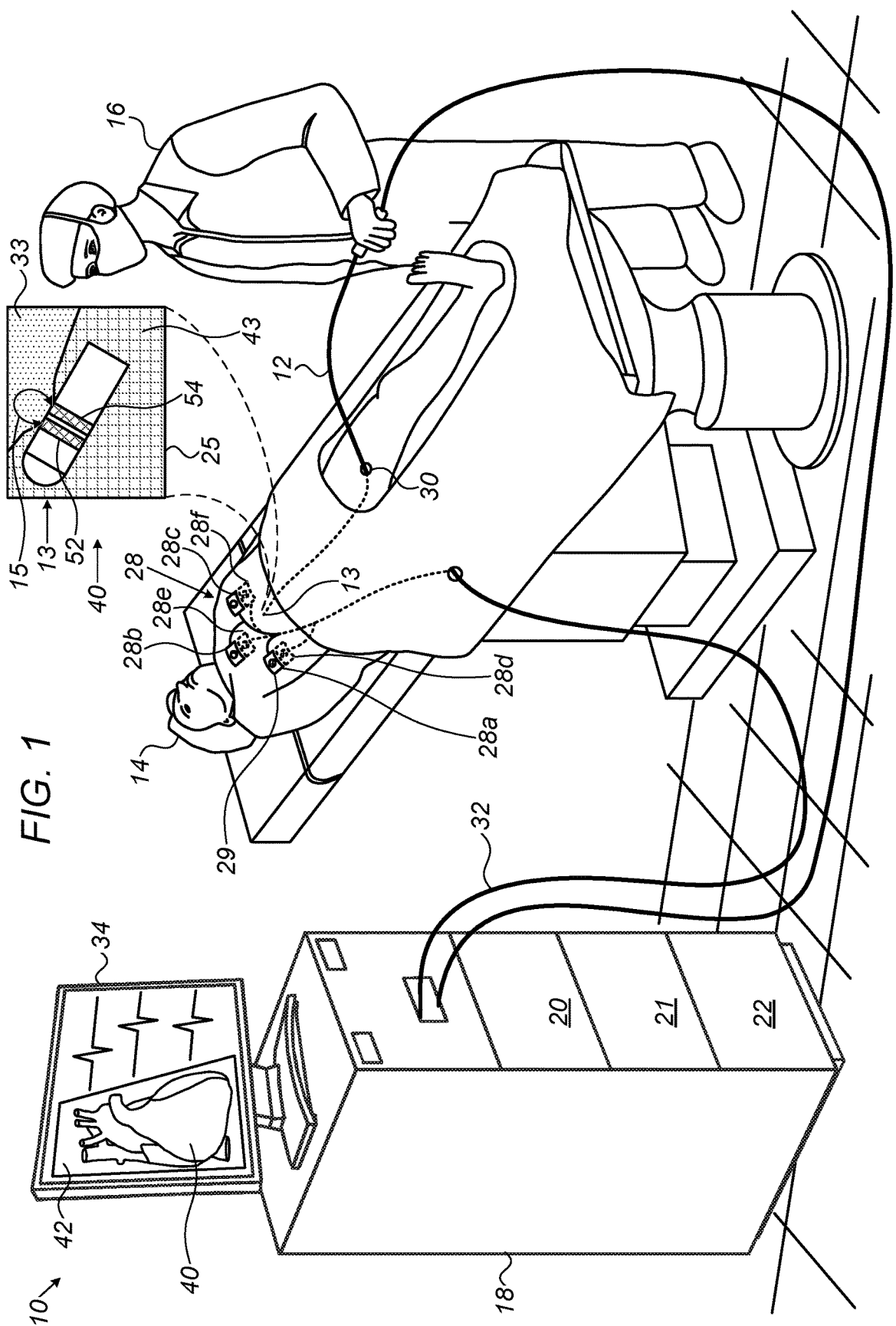
FIG. 1 is a schematic, pictorial illustration of a system for ablating tissue of a patient heart, in accordance with an embodiment of the present invention.

Medical probes, also referred to herein as catheters, are used in a variety of medical procedures, such as in radio-frequency (RF) ablation of heart tissue. When performing an ablation procedure, it is important to ensure physical contact between ablation electrodes of the probe distal tip and the target tissue, so as to form the desired lesion in the tissue and to prevent the formation of byproduct blood clots that may put the patient at risk.

Embodiments of the present invention that are described hereinbelow provide improved techniques for assessing physical contact between a given section of a catheter distal tip and target tissue, e.g., in performing electro-potential (EP) mapping of patient heart, and/or in ablation to the patient heart and/or any other procedure involving physical contact between a catheter distal tip and target tissue.

The distal tip typically comprises one or more pairs of electrodes coupled to the distal tip along the given section. In some embodiments, each pair of electrodes is coupled to a respective current source, which is configured to flow an electrical current having a selected frequency between the electrodes of the pair. The electrodes of each pair are electrically isolated from one another, so that electrical current can flow between the electrodes only when some conductive material such as tissue or blood is in contact with both electrodes.

In some embodiments, the current sources are mounted on a circuit board (CB). The CB further comprises an electronic circuit, such as an application specific integrated circuit (ASIC), which is configured to measure a single-ended voltage between each electrode and ground.

In order to enable a meaningful measurement of the voltage on an electrode (i.e., a voltage that is truly a known function of the current flowing through the electrode), the electrode and the current source should be referenced to a common reference ground.

In some embodiments of the present invention, a common reference ground for the electrodes and the current sources is established using the layout of the CB on which they are mounted. For this purpose, the CB layout is designed to have, at selected frequencies of the current sources, predefined capacitances between the current sources and ground.

For a given electrode, belonging to a given electrode pair, the unipolar voltage develops on the electrode in response to the electrical current flowed through the pair by the respective current source. The predefined capacitance of the layout references the current source to ground, rather than being floating, thereby enabling a meaningful measurement of the unipolar voltage relative to ground potential.

With the common reference ground established, the measured unipolar voltage is indicative of a respective impedance of the tissue or blood that is in physical contact with the pair of electrodes. Since the blood has better electrical conductivity than the tissue, the impedance and therefore the voltage measured between the electrodes is higher when in contact with the tissue than with the blood alone. In some embodiments, based on the measured unipolar voltages, the ASIC is configured to assess whether there is a physical contact between the heart tissue and the given section of the distal tip.

The disclosed techniques improve patient safety in ablation procedures but are not limited to ablation, and can be used, for example, in EP mapping and other procedures. Furthermore, the disclosed techniques increase the functionality and reduce the cost of an ablation catheter by integrating a tissue proximity indicator (TPI) with an impedance-based position tracking system of the catheter.

System Description

FIG. 1 is a schematic, pictorial illustration of a system 10 for ablating tissue of a patient heart 40, in accordance with an embodiment of the present invention. In some embodiments, system 10 supports construction of a mapping of heart 40 of a patient 14, and using the constructed mapping for navigating a medical tool within heart 40, during an ablation procedure.

Reference is now made to an inset 25. In some embodiments, system 10 comprises a medical probe, such as a catheter 12, having a distal tip 13. In some embodiments, distal tip 13 comprises a plurality of devices, such as a pair of electrodes 52 and 54 coupled to respective ends of a given section of the distal tip. In some embodiments, electrodes 52 and 54 may have various roles in distal tip 13. For example, electrodes 52 and 54 may serve as impedance-based position sensors, and/or as electro-potential (EP) sensing electrodes, and/or as ablation electrodes. In this configuration, distal tip 13 of catheter 12 may be used for mapping and/or for ablating tissue 33 of heart 40.

During the mapping phase a physician 16 may insert catheter 12, via an insertion point 30, into vasculature of patient 14, and may then navigate the catheter tip to heart 40. Subsequently, catheter 12 is used for mapping tissue 33 of heart 40 before ablating the tissue.

In the context of the present invention and in the claims, the term "electrical impedance" is also referred to herein simply as "impedance" for brevity.

In some embodiments, an operating console 18 comprises a radiofrequency (RF) generator 22, configured to generate the RF ablation signals applied by catheter 12 to tissue 33 of heart 40.

In some embodiments, console 18 comprises a processor 20, typically a general-purpose computer, with suitable front end and interface circuits for receiving signals from catheter 12 and for controlling other components of system 10 described herein. Processor 20 may be programmed in software to carry out the functions that are used by the system, and the processor stores data for the software in a memory 21. The software may be downloaded to console 18 in electronic form, over a network, for example, or it may be provided on non-transitory tangible media, such as optical, magnetic or electronic memory media. Alternatively, some or all of the functions of processor 20 may be carried out by dedicated or programmable digital hardware components.

In some embodiments, system 10 further comprises an impedance-based active current location (ACL) system, typically used for tracking the position of distal tip 13 for the purpose of navigating catheter 12 to ablation locations within heart 40 of patient 14.

In an embodiment, the position of distal tip 13 is shown on an image 42 of heart 40, which is displayed on a user display 34. In some embodiments, image 42 is acquired using an anatomical imaging system, such as a computerized tomography (CT) system or any other suitable imaging technique.

In some embodiments, the ACL system comprises a plurality of electrodes 28, which are coupled to the body of patient 14, e.g., via patches 29 that adhere to the skin of patient 14. In the example of FIG. 1, system 10 comprises six electrodes, of which electrodes 28a, 28b, and 28c are coupled to the front (e.g., chest) of patient 14, and electrodes 28d, 28e, and 28f are coupled to the back of patient 14. In other embodiments, system 10 may comprise any suitable number of electrodes, coupled to the patient skin in any suitable arrangement.

Electrodes 28 of patches 29 are typically connected, via a cable 32, to processor 20, which is configured to receive, from electrodes 28 and from other sensors information such as values of impedance. Based on this information, processor 20 is configured to estimate the position of distal tip 13 within heart 40.

Display 34, is typically configured to facilitate performance of the mapping and/or ablation procedures by displaying relevant information to physician 16. For example, processor 20 may register between the coordinate systems of an impedance-based position tracking system and the coordinate system of the CT system (which acquired image 42), so as to display the location and orientation of distal tip 13 within image 42.

As noted above, electrodes 28 are typically used for navigating catheter 12 within the body of patient 14, using impedance-based tracking techniques, such as those described, for example, in U.S. Pat. No. 8,456,182 and US Patent Application Publication 2015/0141798, whose disclosures are incorporated herein by reference. Such techniques involve estimating the location and orientation of distal tip 13 responsively to the different impedances measured between distal tip 13 and each of electrodes 28a-28f. As described above, the estimated location of distal tip 13 may be indicated to the physician as a suitable icon on display 34. Based on this indication, physician 16 may navigate distal tip 13 of catheter 12 to one or more target locations within heart 40, and subsequently ablate tissue at one or more of the target locations.

In some embodiments, the location and orientation of distal tip 13 at any given time, are typically estimated by applying an electrical signal of a known amplitude to distal tip 13, and the resulting voltage gradients and/or currents are measured at each pair of electrodes 28. In alternative embodiments, the electrical signal may be applied by electrodes 28, and the resulting electrical values are measured by one or more sensors of distal tip 13.

In some embodiments, these applied electrical signals cause electrodes 28, each of which is located at a different position relative to the catheter, to exhibit different respective electrical values, due to a different amount of electrically-impeding tissue (and therefore, a different degree of impedance) between distal tip 13 and each electrode among electrodes 28.

In some embodiments, these measured electrical values are sent, via cable 32, to processor 20, which uses these values to estimate the relative location and orientation of distal tip 13 relative to electrodes 28 (whose positions are known). Alternatively, voltage gradients between the distal tip of the catheter and the electrodes may be generated, and the resulting currents flowing through the electrodes may be measured and used for estimating the location and orientation of distal tip 13.

In some embodiments, in a calibration procedure referred to herein as "mapping,", processor 20 is configured to construct a set of data points that each comprises the position and electrical values measured at a respective position visited by distal tip 13. In an embodiment, when completed, the mapping is applied (e.g., during ablation) to electrical values acquired by distal tip 13 and/or electrodes 28, for translating measured electrical values into a position measurement in heart 40.

Note that a separate mapping may be constructed for selected respiration operations (for example, after a full inhalation operation, after a full exhalation operation, or a midpoint between inhalation and exhalation operations) of patient 14.

Reference is now made again to inset 25. Before ablating tissue 33, it is important to bring the ablation electrodes of distal tip 13 in physical contact with tissue 33. In some embodiments, system 10 is configured to flow an electrical current to electrodes 52 and 54. In response to the electrical current, a voltage develops between the electrodes, wherein the voltage value depends on whether the electrodes are in contact with the tissue or blood. The ASIC measures for at least one of electrodes 52 and 54 a single-ended voltage, also referred to herein as a unipolar voltage, which is indicative of a physical contact between the given section of distal tip 13 and tissue 33. Further details on the configuration of system 10, which is related to the tissue contact sensing are described in FIG. 2 below As shown in inset 25, distal tip 13 is in physical contact with tissue 33. In this position, electrical current flows through electrical path 15 between electrodes 52 and 54 via tissue 33. When both electrodes are in physical contact with the tissue, this voltage is indicative of an electrical impedance of the tissue, also referred to herein as Z-tissue.

Similarly, when distal tip 13 (i.e., at least one of the electrodes) is not in physical contact with tissue 33, the electrical current flows between electrodes 52 and 54 via blood 43. In this position, the unipolar voltage on at least one of electrodes 52 and 54 (relative to the ground), is indicative of an electrical impedance of the blood, also referred to herein as Z-blood, which is typically significantly smaller than the electrical impedance of tissue 33. In some embodiments, processor 20 or any other processing device, as will be shown in FIG. 2 below, is configured to measure the unipolar voltage and based on the measured voltage, and to assess whether there is physical contact in the section between the respective electrodes (e.g., electrode 52 or 54) of distal tip 13 and tissue 33.

Figure 2:
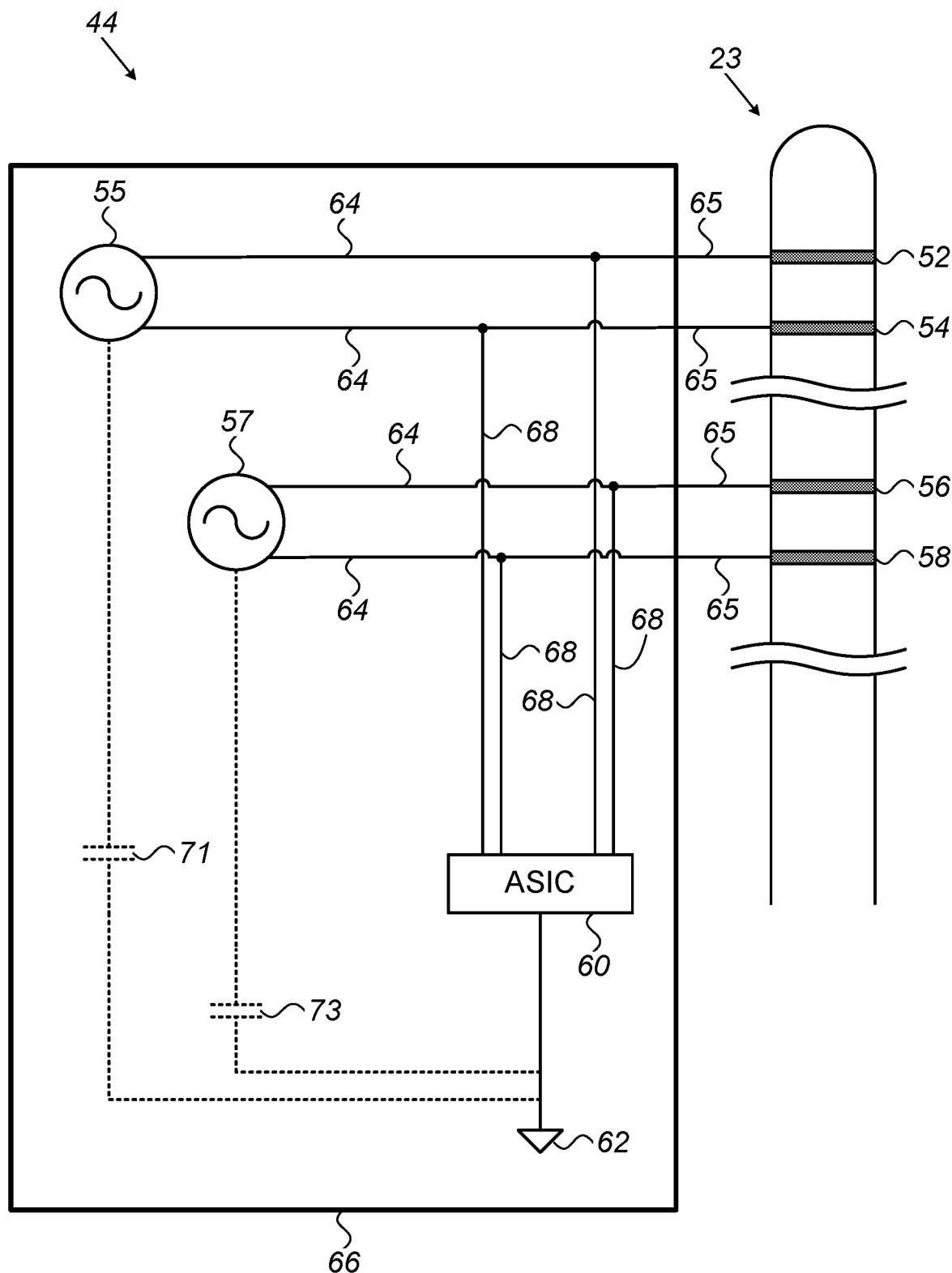
FIG. 2 is a schematic, pictorial illustration of a module for assessing contact between catheter and tissue, in accordance with an embodiment of the present invention.

A Module for Assessing Contact Between Probe and Tissue Using One or More Pairs of Electrodes FIG. 2 is a schematic, pictorial illustration of a module 44 for assessing contact between distal tip 23 and tissue 33, in accordance with an embodiment of the present invention. Distal tip 23 may replace, for example, distal tip 13 of catheter 12 shown in FIG. 1 above.

In some embodiments, module 44 comprises a circuit board (CB) 66, which is electrically coupled, via electrical traces 64, and leads 65 running through the catheter, to electrodes 52, 54, 56 and 58 of distal tip 23. In some embodiments, CB 66 comprises a current source 55, which is configured to flow, via electrodes 52 and 54 of distal tip 23, traces 64 and leads 65, an alternating electrical current having a selected frequency (e.g., 6.3 kHz). As described in FIG. 1 above, the electrical current flows between electrodes 52 and 54 through any electrical path, such as path 15, which is electrically connecting threbetween. In the present example, the electrical current may flow through blood 43 or through tissue 33, each of which has a different impedance.

In some embodiments, current source 55 is electrically connected, via the layout of CB 66, to a ground 62. Note that by design, the layout of CB 66 creates a predefined capacitance, at the selected frequency of current source 55, between the current source and ground 62. This capacitance is shown schematically as a capacitor 71. In this configuration, current source 55 is not floating. Rather, at the selected frequency of the alternating current generated by current source 55, the predefined capacitance is configured to establish ground 62 as a reference ground for current source 55.

In some embodiments, current source 55 is configured to produce a constant electrical current between electrodes 52 and 54, so that the current value does not depend on the impedance between the electrodes. Thus, a respective single-ended voltage is formed between each electrode among electrodes 52 and 54, and ground 62. Note that the voltage on each of electrodes 52 and 54 is indicative of the impedance between electrodes 52 and 54, and therefore is indicative of whether electrodes 52 and 54 are in contact with tissue 33 or with blood 43.

In some embodiments, module 44 further comprises an application specific integrated circuit (ASIC) 60, which is mounted on CB 66 and is electrically coupled to electrodes 52 and 54. In the example of FIG. 2, CB 66 comprises traces

68 that electrically connect, via traces 64 and leads 65, between ASIC 60 and each electrode among electrodes 52 and 54. In other embodiments, module 44 may comprise, in addition to or instead of ASIC 60, any other suitable electronic circuit, which is electrically coupled to electrodes 52 and 54 using any suitable interconnecting configuration.

In some embodiments, ASIC 60 may comprise any suitable IC device, such as a general-purpose processor, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

In some embodiments, ASIC 60 is configured to measure the single-ended voltage relative to ground that is formed on at least one of electrodes 52 and 54, in response to the electrical current of source current 55. As described above, the measured voltage is indicative of the impedance of the electrical path between electrodes 52 and 54. In the example of FIG. 1, the electrical path between the electrodes may pass through tissue 33, blood 43, or through a combination thereof. Thus, based on the measured voltage, ASIC 60 is configured to assess the physical contact between tissue 33 and the one or more respective electrodes of distal tip 13. Note that in the configuration of FIG. 2, the layout of CB 66 is designed to form a reference ground for measurement of the single-ended voltage.

In some embodiments, the single-ended voltage that is formed, for example, on electrode 54 relative to ground 62, provides an indication of whether distal tip 13 is in physical contact with tissue 33 in a section located between electrodes 52 and 54.

In some embodiments, distal tip 13 may comprise additional pairs of electrodes, such as electrodes 56 and 58, located at the ends of another section along distal tip 13. Typically, although not necessarily, the section between electrodes 56 and 58 does not overlap with the section located between electrodes 52 and 54. In these embodiments, a current source 57, which is similar to current source 55, is coupled to electrodes 56 and 58 and is configured to flow an alternating electrical current. Typically, although not necessarily, both current sources 55 and 57 (or all current sensors in the case of more than two pairs of electrodes) have the same frequency. In response to the electrical current, the single-ended voltage relative to ground 62 that is formed on at least one of electrodes 56 and 58, is measured by ASIC 60 as described above.

In an embodiment, the layout of CB 66 is designed in to provide, at the selected frequency, a predefined value of capacitance between current source 57 and ground 62, shown schematically as a capacitor 73.

In another embodiment, current source 57 may be configured to flow an electrical current having a given frequency, different from the selected frequency of current source 55. In this embodiment, the layout of CB 66 is configured to create, at the given frequency, a given capacitance between current source 57 and ground 62. Note that the given capacitance differs from the predefined capacitance and configured to form a common reference ground for measurement of the single-ended voltage that corresponds to the given frequency. In this embodiment, using the techniques described above, ASIC 60 is configured to assess physical contact between tissue 33 and the section of distal tip 23 located between electrodes 56 and 58.

By distributing along distal tip 13 additional pairs of electrodes, such as electrodes 52 and 54 coupled to respective electronic circuitries as described above, module 44 is configured to detect physical contact between each of the respective pairs and tissue 33. In various embodiments, any suitable number of electrode pairs can be used.

In various embodiments, the layout of CB 66 can be designed in various ways to have the desired capacitances (71 and 73) between current sources 55 and 57 and ground 62. The desired capacitances are typically on the order of 50 pF. Such a capacitance can be achieved, for example, by controlling parameters such as (i) the geometrical distance between each current source and the nearest ground line, (ii) the thickness and/or composition of a dielectric layer that separates between a ground layer and a copper layer on which the current sources are fabricated.

In some embodiments, ASIC 60 is configured to hold at least a predefined threshold and, by comparing between the measured unipolar voltage and the predefined threshold, to assess the physical contact between tissue 33 and each electrode among electrodes 52, 54, 56 and 58. If, for a given electrode, the value of the unipolar voltage is larger than the predefined threshold, ASIC 60 may output an indication of physical contact between tissue 33 and the given electrode. Similarly, if the value of the unipolar voltage is equal to or smaller than the predefined threshold, ASIC 60 may output an indication of physical contact between the given electrode and blood 43.

Additionally or alternatively, processor 20 is configured to hold the predefined threshold, and, based on the value of the unipolar voltage measured by ASIC 60 on each electrode among electrodes 52, 54, 56 and 58, to output an indication of whether there is physical contact between each of the electrodes and tissue 33.

In the context of the present invention and in the claims, the term "electronic circuit" refers to any device configured to measure the single-ended voltage relative to ground 62 that is formed on at least one of the electrodes in the pair in response to the electrical current, and, based on the measured voltage, to assess the physical contact between at least one of the respective electrodes and tissue 33. In an embodiment, the voltage measurement and the assessment of the physical contact may be carried out using a single device, such as ASIC 60 of FIG. 2 or processor 20 of FIG. 1. In another embodiment, the voltage measurement may be carried out using one device, e.g., ASIC 60, and the assessment of the physical contact may be carried out using another device, for example by processor 20 that receives the voltage measurements from ASIC 60. Note that in this embodiment, the term "electronic circuit" refers to a combination of ASIC 60 and processor 20. In an alternative embodiment, system 10 may comprise any other suitable configuration for measuring the voltage from the electrodes, and for assessing the physical contact based on the measured voltages.

In an embodiment, processor 20 is further configured to display, e.g., in image 42, distal tip 13 overlaid on the image of heart 40, such that some of the electrodes may be in physical contact with tissue 33 and the remaining electrodes are in physical contact solely with blood 43.

Although the embodiments described herein mainly address cardiac ablation and EP mapping procedures, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   flowing from a current source an electrical current having a selected frequency between a pair of electrodes coupled to a medical probe; and
   measuring, using an electronic circuit, a single-ended voltage relative to ground that is formed on at least one of the electrodes in the pair in response to the electrical current, and, based on the measured voltage, assessing physical contact between the at least one of the electrodes and tissue,
   wherein a circuit board, which comprises the current source and the electronic circuit comprises a physical layout that produces, at the selected frequency of the current source, a predefined capacitance between the current source and ground, thereby establishing the ground as a reference ground for the current source, and referencing the electrodes and the current source to the reference ground established by the predefined capacitance, thus forming a reference for measurement of the single-ended voltage.

2. The method according to claim 1, wherein the electronic circuit comprises an application specific integrated circuit (ASIC).

3. The method according to claim 1, wherein the electrodes of the pair are fixed at opposite ends of a first section of the medical probe, and comprising flowing, from an additional current source, the electrical current between an additional pair of electrodes coupled to opposite ends of a second section of the medical probe, different from the first section, and wherein each of the additional electrodes is electrically coupled to the electronic circuit for assessing physical contact between at least one of the additional electrodes and tissue.

4. The method according to claim 3, and comprising outputting, based on the assessed physical contacts, whether there is physical contact between the tissue and at least one of (i) the electrodes, and (ii) the additional electrodes.

5. The method according to claim 3, wherein the first and second sections are not overlapped with one another.

6. The method according to claim 1, wherein assessing the physical contact comprises indicating that the at least one of the electrodes is in physical contact with the tissue when the measured voltage is above a predefined threshold, and indicating that the at least one of the electrodes is not in physical contact with the tissue when the measured voltage is below the predefined threshold.

* * * * *